US011369651B2

(12) United States Patent
Wang et al.

(10) Patent No.: US 11,369,651 B2
(45) Date of Patent: Jun. 28, 2022

(54) **USES OF FU-LING (*PORIA COCOS*) EXTRACT AND TUMULOSIC ACID IN PROTECTING MUSCLES**

(71) Applicant: SINPHAR PHARMACEUTICAL CO., LTD. (DONGSHAN, TAIWAN), Yilan County (TW)

(72) Inventors: Chao-Jih Wang, Zhejiang (CN); Han-Peng Kuo, Dongshan Township, Yilan County (TW); Ai-Ling Yeh, Dongshan Township, Yilan County (TW)

(73) Assignee: SINPHAR PHARMACEUTICAL CO., LTD. (DONGSHAN, TAIWAN), Yilan County (TW)

( * ) Notice: Subject to any disclaimer, the term of this patent is extended or adjusted under 35 U.S.C. 154(b) by 311 days.

(21) Appl. No.: 15/487,545

(22) Filed: Apr. 14, 2017

(65) Prior Publication Data

US 2017/0296603 A1    Oct. 19, 2017

Related U.S. Application Data

(60) Provisional application No. 62/322,406, filed on Apr. 14, 2016.

(30) Foreign Application Priority Data

Apr. 13, 2017   (TW) ................. 106112372

(51) Int. Cl.
*A61K 36/076* (2006.01)
*A61K 31/191* (2006.01)

(52) U.S. Cl.
CPC .......... *A61K 36/076* (2013.01); *A61K 31/191* (2013.01)

(58) Field of Classification Search
CPC ............................ A61K 36/076; A61K 31/191
See application file for complete search history.

(56) References Cited

U.S. PATENT DOCUMENTS

2009/0318399 A1 * 12/2009 Lin ..................... A61K 31/56
514/180

FOREIGN PATENT DOCUMENTS

| CN | 101095938 A | * | 1/2008 | |
|----|-------------|---|--------|---|
| CN | 101095938 A | | 2/2008 | |
| CN | 101352514 A | | 1/2009 | |
| CN | 104825525 A | | 8/2015 | |
| CN | 104958305 A | * | 10/2015 | |
| EP | 2246047 A1 | * | 11/2010 | .......... A61K 31/575 |
| KR | 100592488 B1 | * | 6/2006 | |
| TW | 201039832 A1 | | 11/2010 | |
| WO | WO 2014/162925 A1 | | 10/2014 | |

OTHER PUBLICATIONS

Zhao, Xiao-Ping et al., "Review of the Mechanisms of Chinese Medicine FU-LING (*Poria cocos*) Against Exercise Fatigue," *Science & Technology Information*, No. 16, p. 67 (2011).
Zhang, Xian-Shu et al., "Research Progress of the Pharmacological Effects and Clinical Applications of Triterpenes from FU-LING (*Poria cocos*)," *Journal of Chongqing Industry & Trade Polytechnic*, No. 4 (2011).
Database WPI, Week 200839, Thomson Scientific, London, GB, XP002795721, An 2008-G05097 & CN 101095938 A, Beijing Yixintang Medical Rest. Inst., *abstract*, 2 pages (Jan. 2, 2008).
Li, Weifeng, et al., "Polysaccharides from *Poria cocos* (PCP) inhibits ox-LDL-induced vascular smooth muscle cells proliferation and migration by suppressing TLR4/NF-κB P65 signaling pathway," *Journal of Functional Foods*, vol. 60, 11 pages (2019).
Ríos, José-Luis, "Chemical Constituents and Pharmacological Properties of *Poria cocos*," *Planta Medica*, vol. 77, No. 7, pp. 681-691 (2011).
Common Chinese Medicine Pharmacology and Clinical Application, pp. 163-164 (2005).
Fang, Liang, et al., "Effect of Sijunzi Decoction on Skeletal Muscle Atrophy and Some Inflammatory Cytokines in Lung Cancer Cachexia Mice," *Liaoning Zhongyi Zazhi*, 39(7), pp. 1263-1265 (2012).

\* cited by examiner

*Primary Examiner* — Amy L Clark
(74) *Attorney, Agent, or Firm* — Christensen, Fonder, Dardi & Herbert PLLC

(57) ABSTRACT

A method for protecting muscles, comprising administering to a subject in need an effective amount of a FU-LING (*Poria cocos*) extract, tumulosic acid and/or a pharmaceutical acceptable salt of tumulosic acid. In particular, the method of the present invention is for protecting muscle cells against injury, promoting regeneration and repair of muscle, regulating, treating and/or delaying muscle atrophy (especially caused by aging, diseases, and cachexia), or helping normal muscle contraction, maintaining normal muscle physiology, maintaining normal neuromuscular function, maintaining normal energy metabolism, or enhancing energy level.

9 Claims, 2 Drawing Sheets

USES OF FU-LING (*PORIA COCOS*) EXTRACT AND TUMULOSIC ACID IN PROTECTING MUSCLES

CROSS-REFERENCES TO RELATED APPLICATIONS

This application claims priority from U.S. Provisional Application Ser. No. 62/322,406 filed on Apr. 14, 2016 with the United States Patent and Trademark Office; the disclosures of which are incorporated herein in their entirety by reference.

FIELD OF THE INVENTION

The present invention relates to the uses of a FU-LING (*Poria cocos*) extract and tumulosic acid (i.e., an ingredient of the FU-LING extract) or a pharmaceutically acceptable salt of tumulosic acid. The invention especially relates to the use of the FU-LING extract, tumulosic acid or a pharmaceutically acceptable salt of tumulosic acid in protecting muscles. This includes protecting muscle cells against injury, promoting the regeneration and repair of muscles and thereby regulating, treating, and/or delaying muscle atrophy, especially muscle atrophy caused by aging, diseases, and/or cachexia.

BACKGROUND OF THE INVENTION

Muscle tissue is the most abundant tissue in mammals, and is mainly responsible for generating force to cause movement of various parts of the body. Muscle can be divided into three groups: skeletal muscle, cardiac muscle and smooth muscle. Based on the metabolic types and characteristics, skeletal muscle can be divided into slow twitch muscle and fast twitch muscle, wherein the former consists of slow-twitch fiber proteins that can twitch for a longer period, but the generated force is weaker; and the latter consists of fast-twitch fiber proteins that can twitch faster and stronger than the former, but fatigues more easily.

Under normal physiological conditions, there is a dynamic balance between the synthesis and degradation of muscle proteins. However, when an imbalance in muscle protein metabolism occurs (namely, the degradation rate of muscle proteins become greater than the synthesis rate), it causes muscle atrophy (or the loss of muscle) and leads to characteristic changes, such as a decrease in muscle mass, a reduction of muscle fiber cross-sectional area, and a selective reduction of muscle fiber type-related proteins (i.e., slow-twitch fiber proteins and fast-twitch fiber proteins), which can result in symptoms that seriously affect daily work and vital function, including a reduction in muscle strength, movement disorders, fatigue, metabolic disturbances, etc.

In general, the injured position of skeletal muscle can be repaired through a muscle regeneration process. However, when the regeneration process is severely hampered, muscle atrophy occurs. Research has found that the muscle regeneration process is quite complex, first involving the activation of satellite cells followed by differentiating the activated satellite cells into mononucleated myoblasts. The mononucleated myoblasts further proliferate and differentiate to fuse into multinucleated myotubes, and finally, mature myotubes differentiate into new myofibers. Different stages of muscle regeneration are respectively regulated by different myogenic regulatory factors (MRFs). For example, in the process of myoblasts differentiating into myotubes, MyoD and myogenin can regulate the formation of myosin heavy chain (MyHC, a myotube-specific structure protein). The aforementioned regulation is an important step in muscle regeneration, therefore, MyoD, myogenin and MyHC can be used as markers for myoblast differentiation.

It is known that some physiological conditions or specific diseases can cause muscle cell injury, leading to a muscle protein metabolic imbalance or apoptosis of muscle cells, and ultimately, cause muscle atrophy. Physioloical conditions causing muscle atrophy include, for example, neurodegeneration, long-term bed rest, aging, diseases, cachexia (e.g., cancer cachexia), etc.; and specific diseases causing muscle atrophy include sepsis, acquired immune deficiency syndrome (AIDS), renal failure, Cushing syndrome (CS), sarcopenia, cancer, chronic obstructive pulmonary disease (COPD), congestive heart failure (CHF), etc.

Aging is the major factor causing sarcopenia. Statistical data indicate that the incidence rate of sarcopenia among those aged 60 to 70 is 13 to 24%, while the incidence rate of sarcopenia among people older than 80 years of age is about 50%. In America, the medical cost caused by sarcopenia per year is about 11.8 to 26.2 billion USD. While cachexia relates to other diseases with high incidence rates, for example, about 50% of patients with cancer, 20 to 40% of patients with COPD, and 50 to 70% of patients with CHF will exhibit the symptoms of cachexia (e.g., dystrophy).

In clinical practice, there is still a lack of an effective method for treating or delaying muscle atrophy. Therefore, to try to develop a more effective method for treating or delaying muscle atrophy, the inventors of the present invention selected FU-LING from traditional herbs, and then investigated the feasibility of using FU-LING in protecting muscle (namely, protecting muscle cells against injury and promoting the regeneration and repair of muscles).

The inventors of the present invention found that the FU-LING extract and tumulosic acid contained therein are effective in protecting muscle cells against injury and promoting the regeneration and repair of muscles. Therefore, the FU-LING extract and tumulosic acid can be used for regulating, treating and/or delaying muscle atrophy, especially for regulating, treating and/or delaying muscle atrophy caused by aging, disease and/or cachexia, and thus can be used for providing a pharmaceutical composition, a medicament or a food product that protect muscles.

SUMMARY OF THE INVENTION

An objective of the present invention is to provide a use of FU-LING extract in the manufacture of a medicament or a food product for protecting muscles. The FU-LING extract is preferred to be a polar solvent extract of FU-LING wherein the polar solvent is selected from the group consisting of water, C1-C4 alcohols, and combinations thereof. More preferably, the FU-LING extract comprises tumulosic acid. It is more preferred for the FU-LING extract to refer to an extract of FU-LING meat, an extract of FU-LING epidermis and/or an extract of FU-LING fermentation product. The medicament is used for protecting muscle cells against injury, promoting the regeneration and repair of muscles, or for treating and/or delaying muscle atrophy caused by at least one of the following: aging, disease, and cachexia. The food product is used for regulating muscle atrophy caused by at least one of the following: aging, disease, and cachexia, and thereby is useful for helping normal muscle contraction, maintaining normal muscle physiology, maintaining normal neuromuscular function, maintaining normal energy metabolism, or enhancing energy level. The food product is a health food, a nutritional supplement food or a special nutrition food.

Another objective of the present invention is to provide the use of an active ingredient in the manufacture of a medicament or a food product for protecting muscles, wherein the active ingredient is tumulosic acid and/or a pharmaceutically acceptable salt of tumulosic acid. The active ingredient is preferred to be used in the form of a plant extract; more preferably, the active ingredient is used in the form of a FU-LING extract, (e.g., the extract of FU-LING meat, FU-LING epidermis and/or FU-LING fermentation product) especially a polar solvent extract of FU-LING wherein the polar solvent is selected from the group consisting of water, C1-C4 alcohols, and combinations thereof. The medicament is used for protecting muscle cells against injury, promoting the regeneration and repair of muscles, or for treating and/or delaying muscle atrophy caused by at least one of the following: aging, disease, and cachexia. The food product is used for regulating muscle atrophy caused by at least one of the following: aging, disease, and cachexia, and thereby is useful for helping normal muscle contraction, maintaining normal muscle physiology, maintaining normal neuromuscular function, maintaining normal energy metabolism, or enhancing energy level. The food product is a health food, a nutritional supplement food or a special nutrition food.

Still another objective of the present invention is to provide a method for protecting muscles, comprising administering to a subject in need an effective amount of a FU-LING extract. The method is for protecting muscle cells against injury, promoting the regeneration and repair of muscles, and for regulating, treating, and/or delaying muscle atrophy caused by at least one of the following: aging, disease, and cachexia. The method is also for helping normal muscle contraction, maintaining normal muscle physiology, maintaining normal neuromuscular function, maintaining normal energy metabolism, or enhancing energy level.

Still yet another objective of the present invention is to provide a composition for protecting muscles, wherein the composition is a medicament or a food product comprising an effective amount of the FU-LING extract. The composition is for protecting muscle cells against injury, and for regulating, treating, and/or delaying muscle atrophy caused by at least one of the following: aging, disease, and cachexia. is the composition is also for helping normal muscle contraction, maintaining normal muscle physiology, maintaining normal neuromuscular function, maintaining normal energy metabolism, or enhancing energy level.

The detailed technology and some particular embodiments implemented for the present invention are described in the following paragraphs for people skilled in the field to well appreciate the features of the claimed invention.

DESCRIPTION OF THE PREFERRED EMBODIMENT

Figure 1:
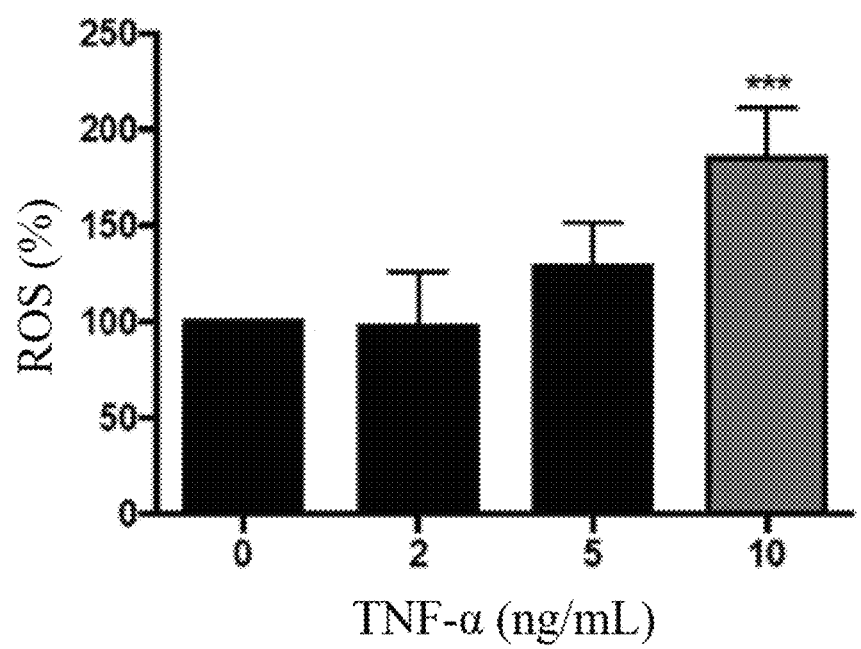
FIG. 1 illustrates the effects of Tumor necrosis factor-α (TNF-α) on intracellular reactive oxidative stress (ROS) of C2C12 cells.

The detailed technology and preferred embodiments implemented for the present invention are described in the following paragraphs for people skilled in the field to well appreciate the features of the claimed invention. However, the present invention may be realized in various embodiments without departing from the spirit of the present invention, and the present invention should not be considered to be limited to the embodiments described in the specification.

In addition, unless otherwise stated herein, the expressions "a," "the" or the like recited in the specification of the present invention (especially in the claims) should be interpreted to include both the singular and plural forms. Furthermore, the term "an effective amount" used in this specification refers to the amount of the compound that can at least partially alleviate the condition that is being treated in a suspected subject when administered to the subject. The unit "mg/kg-body weight" refers the dosage in mg required per kg of body weight.

In addition, unless otherwise stated herein, the term "subject" recited in the specification of the present invention (especially in the claims) refers to a mammalian, including human and non-human animals. The terms "treat" and "treating" cover the prevention of particular diseases or disorders, the amelioration of particular diseases or disorders, and/or the prevention or elimination of the diseases or disorders. The term "regulating muscle atrophy" refers to helping normal muscle contraction, maintaining normal muscle physiology, maintaining normal neuromuscular function, maintaining normal energy metabolism and/or enhancing energy level. The term "pharmaceutically acceptable salt" refers to salts that can produce pharmacological activities that are the same as or similar to those produced by their parent compound after being administrated to an organism and that are physiologically tolerable (i.e., with a toxicity as low as possible).

The numerical ranges (e.g., 5 to 100) used in this specification should be construed to include all of the rational numbers in the range consisting of any rational numbers in the range. Therefore, the numerical ranges used in this specification should include all the possible combinations of numerical values between the lowest value and the highest value listed therein. In addition, the word "about", "approximately" or "almost" as used herein substantially represents values within ±20% of the stated value, preferably within ±10% and more preferably within ±5%.

Herbal FU-LING refers to the dried sclerotium of *Poria cocos* (Schw.) Wolf, a fungus in the family Fomitopsidaceae. *Poria cocos* fungus often parasitizes on the roots of pine trees. FU-LING is of a light brown or dark brown color at the external layer (epidermis of the FU-LING) and of pink or white color at the inner part (meat of the FU-LING).

The inventors of the present invention found that the FU-LING extract can effectively protect muscle cells against injury, and promote the regeneration and repair of muscles. Thus, the FU-LING extract can be used for protecting muscles and has the effect of regulating, treating and/or delaying muscle atrophy. Without being limited by the theory, it is believed that the FU-LING extract used in the present invention can effectively regulate, treat, and/or delay muscle atrophy caused by at least one of the following: aging, disease, and/or cachexia. Therefore, the present invention provides uses of the FU-LING extract in protecting muscles, comprising the use of the FU-LING extract in the manufacture of a medicament or a food product for protecting muscles, a method for protecting muscles comprising administrating the FU-LING extract to a subject in need, and a food product or a pharmaceutical composition comprising the FU-LING extract.

According to the present invention, the FU-LING extract used can be a liquid extract provided by the use of a polar solvent to extract the FU-LING raw material. Wherein the FU-LING raw material can be the FU-LING meat, FU-LING epidermis and/or FU-LING fermentation product; the polar solvent can be water and/or a C1-C4 alcohol. The polar solvent is preferably water, ethanol, or a combination thereof. The amount of the polar solvent and FU-LING may be optionally adjusted. In general, the amount of the polar solvent is not particularly limited as long as the raw material can be uniformly dispersed. In a specific embodiment of the present invention, ethanol is used as the polar solvent, and the raw material is dispersed in ethanol (raw material: ethanol=1:8 in volume) to perform the extraction.

In the above extraction procedure, the extraction is performed for a period of time to achieve the desired degree of extraction. For example, while using ethanol as the polar solvent, the extraction time is usually at least 1 hour, preferably at least 2 hours, more preferably at least 3 hours. The extraction procedure can be optionally supplemented with, for example, boiling, cooling, filtering, concentration by vacuum, resin column chromatography and other operations.

Optionally, alkalization treatment and acidification treatment can be performed sequentially to the liquid extract provided by extraction of FU-LING raw material using a polar solvent to enhance the tumulosic acid content in the liquid extract. The term "alkalization" refers to the use of any suitable alkaline substances to increase the pH value of the material (referring to the liquid extract provided by the extraction of FU-LING raw material using a polar solvent in the present invention). In a specific embodiment of the present invention, sodium hydroxide is used to perform the alkalization reaction.

In general, the pH of the material is increased to not less than about 10 in the alkalization treatment step, preferably to about not less than about 11; most preferably to not less than about 12. In a specific embodiment of the present invention, 1N sodium hydroxide is added to increase the pH of the liquid extract to about 12 in the alkalization treatment. After increasing the pH of the liquid extract, the alkalization reaction is performed at an elevated temperature as necessary. For example, the alkalization reaction is performed at a temperature of not less than 50° C., preferably at a temperature of not less than 60° C. As shown in the appended examples, the alkalization reaction can be performed at a temperature of, for example, about 70° C.

The term "acidification" refers to the use of any suitable acidic substance to reduce the pH of the material (referring to the above alkalized liquid extract in the present invention). In a specific embodiment of the present invention, hydrochloric acid is used to reduce the pH of the alkalized liquid extract.

In general, there is no particular requirement for the degree of pH reduction of the acidification treatment as long as the pH is reduced. For example, the pH of the liquid extract is reduced by at least about 3.0, preferably at least about 4.0. In a specific embodiment of the present invention, the pH of the alkalized liquid extract is reduced to about 7 in the acidification treatment.

The FU-LING extract used in accordance with the present invention can also be a dry substance which can be provided by drying the aforementioned liquid extract obtained by the alkalization and acidification treatment or without alkalization and acidification treatment. To achieve maximum extraction efficiency, FU-LING raw material can be extracted repeatedly using the same or a different polar solvent as necessary. The extracted liquid extract can be combined, and then be dried, or optionally be basified or acidified. Each extraction process can be performed using the same or a different polar solvent.

The inventors of the present invention further found that, among all of the ingredients of the FU-LING extract, tumulosic acid itself can effectively promote the regeneration and repair of muscles, thus can be used for protecting muscles and has the effect of regulating, treating and/or delaying muscle atrophy. As shown in the appended examples, without being limited by the theory, it is believed that tumulosic acid can effectively regulate, treat, and/or delay muscle atrophy caused by at least one of the following: aging, disease, and/or cachexia. Therefore, the present invention also provides uses of tumulosic acid and/or a pharmaceutically acceptable salt of tumulosic acid in protecting muscles, comprising the use of tumulosic acid and/or a pharmaceutically acceptable salt of tumulosic acid in the manufacture of a medicament or a food product for protecting muscles, a method of protecting muscles comprising administrating tumulosic acid and/or a pharmaceutically acceptable salt of tumulosic acid to a subject in need, and a food product or a pharmaceutical composition comprising tumulosic acid and/or a pharmaceutically acceptable salt of tumulosic acid.

The tumulosic acid and/or a pharmaceutically acceptable salt of tumulosic acid are preferably used in the form of a plant extract; and more preferably used in the form of a FU-LING extract, especially in the form of a polar solvent extract of FU-LING, wherein the polar solvent is selected from the group consisting of water, C1-C4 alcohols, and combinations thereof.

Depending on the desired administration manner, the pharmaceutical composition or medicament according to the present invention may be provided in any suitable form without specific limitations. For example, the pharmaceutical composition or medicament can be administered by an oral or parenteral (such as subcutaneous, intravenous, intramuscular, peritoneal, or nasal) route to a subject in need to treat, and/or delay muscle atrophy caused by aging, disease and/or cachexia, but administration is not limited thereby. Depending on the form and purpose, suitable carriers can be chosen and used to provide the pharmaceutical composition or medicament, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the pharmaceutical composition or medicament provided by the present invention may comprise any pharmaceutically acceptable carrier that will not adversely affect the desired effects of the active ingredient (i.e., the FU-LING extract or tumulosic acid). For example, the pharmaceutically acceptable carrier can be water, saline, dextrose, glycerol, ethanol or its analogs, cellulose, starch, sugar bentonite, and combinations thereof. The pharmaceutical composition or medicament can be provided in any suitable form for oral administration, such as in the form of a tablet (e.g., dragee), a pill, a capsule, granules, a pulvis, a fluidextract, a solution, syrup, a suspension, a tincture, etc.

As for the form of injection or drip suitable for subcutaneous, intravenous, intramuscular, or peritoneal administration, the pharmaceutical composition or medicament provided by the present invention may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the pharmaceutical composition or medicament as an intravenous infusion, an emulsified intravenous infusion, a powder for injection, a suspension for injection, or a powder suspension for injection, etc. Alternatively, the pharmaceutical composition or medicament may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the medicament provided by the present invention may further comprise a suitable amount of additives, such as a flavoring agent, a toner, or a coloring agent for enhancing the palatability and the visual perception of the pharmaceutical composition or medicament, and a buffer, a conservative, a preservative, an antibacterial agent, or an antifungal agent for improving the stability and storability of the pharmaceutical composition or medicament. In addition, the pharmaceutical composition or medicament may optionally further comprise one or more other active ingredient(s) (such as vitamin D, vitamin B1, vitamin B2, nicotine, biotin, pantothenic acid, calcium, iodine, magnesium, zinc, proteins, etc.), or be used in combination with a medicament comprising one or more other active ingredients, to further enhance the effects of the pharmaceutical composition or medicament, or to increase the application flexibility and adaptability of the preparation thus provided, as long as the other active ingredients do not adversely affect the desired effects of the active ingredient of the present invention (i.e., the FU-LING extract or tumulosic acid).

Depending on the need, age, body weight, and health conditions of the subject, the pharmaceutical composition or medicament provided by the present invention may be dosed at various administration frequencies, such as once a day, multiple times a day, or once every few days, etc. For example, when the pharmaceutical composition or medicament is administered orally to a subject for protecting muscles, the dosage of the pharmaceutical composition or medicament, as a FU-LING extract, is about 0.003 mg/kg-body weight to about 30 mg/kg-body weight per day, preferably about 0.05 mg/kg-body weight to about 20 mg/kg-body weight per day, and more preferably about 1 mg/kg-body weight to about 15 mg/kg-body weight per day. Alternatively, the dosage of the pharmaceutical composition or medicament, as tumulosic acid, is about 0.5 mg/kg-body weight to about 20 mg/kg-body weight per day, preferably about 1 mg/kg-body weight to about 15 mg/kg-body weight per day, and more preferably about 5 mg/kg-body weight to about 10 mg/kg-body weight per day.

The food product according to the present invention is useful for helping normal muscle contraction, maintaining normal muscle physiology, maintaining normal neuromuscular function, maintaining normal energy metabolism, or enhancing energy level, and can be used for regulating muscle atrophy caused by aging, disease and/or cachexia.

The food product according to the present invention could be a health food, a nutritional supplement food or a special nutrition food, and it may be provided as dairy products, meat products, breadstuff, pasta, cookies, troche, capsule, fruit juices, teas, sport drinks, nutritional drinks, etc., but is not limited thereby. Preferably, the food product according to the present invention is a health food.

Depending on the recommended daily dosage for the age, body weight and health conditions of the subject, the health food, nutritional supplement food and special nutrition food provided by the present invention can be taken at various frequencies, such as once a day, several times a day or once every few days, etc. The amount of the FU-LING extract or tumulosic acid in the health food, nutritional supplement food and special nutrition food provided by the present invention can be adjusted, preferably to the amount that should be taken daily, depending on the specific population.

The recommended daily dosage, use standards and use conditions for a specific population (e.g., person with considerable exercises, pregnant women, cancer patients, and heart failure patients), or the recommendations for a use in combination with another food product or medicament can be indicated on the exterior package of the health food, nutritional supplement food and/or special nutrition food provided by the present invention. Thus, it is suitable for the user to take the health food, nutritional supplement food and/or special nutrition food by him- or herself safely and securely without the instructions of a doctor, pharmacist, or related advisor.

The present invention further provides a method for protecting muscles, comprising administering to a subject in need of an effective amount of an active ingredient, wherein the active ingredient is a FU-LING extract, tumulosic acid and/or a pharmaceutically acceptable salt of tumulosic acid. In the method for protecting muscles according to the present invention, the applied route, applied form, suitable dosage and use of the active ingredient in related treatment are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

Example 1

Preparation and Ingredient Analysis of the FU-LING Extract (1-1)
Herbal FU-LING (habitat: Yunnan, China) was washed and its skin was peeled (hereinafter refered to as "FU-LING epidermis"), and the rest was meat part (hereinafter refered to as "FU-LING meat").

(1-2)
700 kg of the FU-LING meat obtained from (1-1) was soaked in 75% ethanol (FU-LING:75% ethanol=1:8 in volume) at room temperature for 12 hours, and then stewed for 3 hours to provide a liquid extract. The foregoing extraction procedures were repeated three times. The liquid extracts obtained from the three extractions were combined and filtered to remove insolubles and provide a filtrate. The ethanol contained in the filtrate was removed by vacuum to provide a concentrated solution. The concentrated solution was spray-dried by a spray dryer to provide a FU-LING extract.

(1-3)
The components of the extract obtained from (1-2) were detected by LC/UV/MS (liquid chromatography coupled to diode array UV detection and mass spectrometry) at 243 nm and 210 nm wavelength, respectively. The results showed that the extract obtained from (1-2) comprised pachymic acid, dehydropachymic acid, tumulosic acid, dehydrotumulosic acid, polyporenic acid C and 3-epi-dehydrotumulosic acid, etc. Then, the content of each component in the extract was quantified by high performance liquid chromatography (HPLC), and the results are shown in Table 1.

TABLE 1

|  | Pachymic acid | Dehydro-pachymic acid | Tumulosic acid | Dehydro-tumulosic acid | Poly-porenic acid C | 3-epi-dehydro tumulosic acid |
|---|---|---|---|---|---|---|
| Content in the extract (%) | 7.07 | 2.54 | 7.47 | 3.76 | 1.63 | 1.02 |

(1-4)

3250 g of the FU-LING extract obtained from (1-2) was uniformly dispersed in pure water (FU-LING:pure water=1:10 in volume). Then, sodium hydroxide was added to provide the mixture with an alkali concentration of 1N (i.e., the pH of the mixture was increased to about 12). The mixture was poured into a mixing barrel which maintained at 70° C. and was stirred uniformly until the reaction was complete. Then, the mixture was neutralized with 12N concentrated hydrochloric acid to decrease the pH of the mixture to 7 and centrifuged at 1000 rpm (by flatbed centrifuge) at room temperature for 30 minutes to remove the filtrate, and the remaining insoluble was washed with pure water. The insoluble was dried and ground to a powder, followed by extraction with 95% ethanol (insoluble:95% ethanol=1:40 in volume). The extraction procedures were repeated three times. The liquid extracts obtained from the three extractions were combined and then concentrated by vacuum to remove ethanol to obtain 2000 g of the product (namely, FU-LING meat extract used in subsequent experiments).

(1-5)

The components of the extract obtained from (1-4) were detected by LC/UV/MS at 243 nm and 210 nm wavelength, respectively. The results showed that the extract obtained from (1-4) comprised tumulosic acid, dehydrotumulosic acid, polyporenic acid C and 3-epi-dehydrotumulosic acid, etc, but did not comprise pachymic acid and dehydropachymic acid. Then, the content of each component in the extract was quantified by high performance liquid chromatography. The results showed that the total content of tumulosic acid, dehydrotumulosic acid, polyporenic acid C and 3-epi-dehydrotumulosic acid in the extract obtained from (1-4) was 6.2% by weight. Among them, tumulosic acid accounted for about 53.74%, dehydrotumulosic acid for about 21.26%, polyporenic acid C for about 12.10% and 3-epi-dehydrotumulosic acid for about 12.90% by weight respectively.

(1-6)

The FU-LING epidermis obtained from (1-1) was soaked in 75% ethanol (FU-LING epidermis:75% ethanol=1:8 by volume) at room temperature for 12 hours, and then stewed for 3 hours to provide a liquid extract. The foregoing extraction procedures were repeated three times. The liquid extracts obtained from the three extractions were combined and filtered to remove the insoluble and provide a filtrate. The ethanol contained in the filtrate was removed by vacuum to provide a concentrated solution. The concentrated solution was spray-dried by a spray dryer to provide a FU-LING epidermis extract for the subsequent experiments.

(1-7)

The FU-LING strains was inoculated in a sterilized solid matrix and fermented in the dark at 20 to 35° C. and a relative humidity of 30 to 70% for several weeks to several months to obtain a FU-LING fermentation product. 100 g of the above FU-LING fermentation product was dried and ground to a powder, and then was uniformly dispersed in 75% ethanol (powder of the fermentation product:75% ethanol=1:8 by volume) at room temperature for 12 hours, and then stewed for 3 hours to provide a liquid extract. The foregoing extraction procedures were repeated three times. The liquid extracts obtained from the three extractions were combined and filtered to remove insolubles and provide a filtrate. The ethanol contained in the filtrate was removed by vacuum to provide a concentrated solution. The concentrated solution was spray-dried by a spray dryer to provide a FU-LING fermentation extract for the subsequent experiments.

Example 2

Establishment of a Model of Muscle Cell Injury

Tumor necrosis factor-α (TNF-α) is a pro-inflammatory cytokine with a molecular weight of 17,000. Human clinical data show that the level of TNF-α increases in patients with special diseases (e.g., cancer, AIDS or COPD), patients using anti-cancer drugs, and the elderly, which is also associated with an increase in muscle catabolism (i.e., the decomposition and consumption of muscle) or muscle cell apoptosis. It was found by researchers that the increase of TNF-α level in an animal body by injecting TNF-α or a drug would induce muscle cell injury (including the metabolic imbalance of muscle protein, muscle cell apoptosis, etc.), and further cause muscle atrophy. To investigate the effects and mechanisms of the FU-LING extract and the ingredients therein on protecting muscles, the inventors of the present invention established a muscle cell injury model with TNF-α.

Firstly, C2C12 cells (i.e., myoblasts of mice, purchased from ATCC) were cultured in H-DMEM medium (purchased from Sigma company) until 80% confluence was attained (i.e., the mixed cell monolayer comprised 80% of the area). Thereafter, the cells were separated into four groups, and the mediums of all the groups were replaced by differentiation mediums supplemented with 2% horse serum. TNF-α (purchased from Sigma company) was then added into those mediums to provide final concentrations of 0, 2, 5 or 10 ng/mL respectively. After being co-treated with the differentiation medium and TNF-α for 4 days, the intracellular reactive oxidative stress (ROS) of the C2C12 cells was measured to serve as the index for model evaluation. Accordingly, a TNF-α induced muscle cell injury model was established. Finally, the group that was not treated with TNF-α (i.e., the concentration of TNF-α was 0 ng/mL) served as a basis for calculating the relative intracellular ROS of the other groups. The results are shown in FIG. 1 (all the data are presented as average values±SEM, n=6, analyzed with a t-test, ***$p<0.001$).

As shown in FIG. 1, the ROS of the C2C12 cells treated with 5 ng/mL of TNF-α increased; and the ROS of the C2C12 cells treated with 10 ng/mL of TNF-α significantly increased. Therefore, 10 ng/mL was chosen as the experimental concentration of TNF-α for inducing muscle cell injury in the following experiments.

Example 3

Effects of the FU-LING Extract on Protecting Muscle Cells Against Injury

The FU-LING extract obtained from Example 1 (1-4) was formulated as a FU-LING meat extract solution in dimethyl sulfoxide (DMSO; purchased from Sigma). After 80% confluence of cells was attained in H-DMEM medium, cells were separated into five groups and treated as follows:
(1) Control group: Cells were cultured in H-DMEM medium (with no FU-LING extract) for 6 hours; thereafter, the medium was replaced by a differentiation medium supplemented with 2% horse serum, and the cells were cultured for 4 days.
(2) TNF-α group: Cells were cultured in H-DMEM medium for 6 hours; thereafter, the medium was replaced by a differentiation medium supplemented with 2% horse serum, and TNF-α was then added into the medium (the final concentration was 10 ng/mL) to perform a co-treatment for 4 days.
(3) TNF-α+ FU-LING extract group (3 groups): The FU-LING extract solution was added into H-DMEM mediums to provide final concentrations of 1, 5 or 10 μg/mL, respectively. The cells were pre-treated with the above mediums for 6 hours. Thereafter, the mediums were replaced by differentiation mediums supplemented with 2% horse serum, and TNF-α was then added into the mediums (the final concentration was 10 ng/mL) to perform co-treatments for 4 days.

The survival rate (tested in MTT assay) and intracellular ROS of the C2C12 cells in each group were measured. The control group served as a basis for calculating the relative survival rates and intracellular ROS of the other groups to evaluate the effective concentration of the FU-LING extract on protecting the TNF-α induced muscle cell injury. The results are shown in FIGS. 2 and 3 (all the data are presented as average values±SEM, n=6, analyzed with a t-test, #p<0.05, ###p<0.001, *p<0.05, ***p<0.001).

Figure 2:
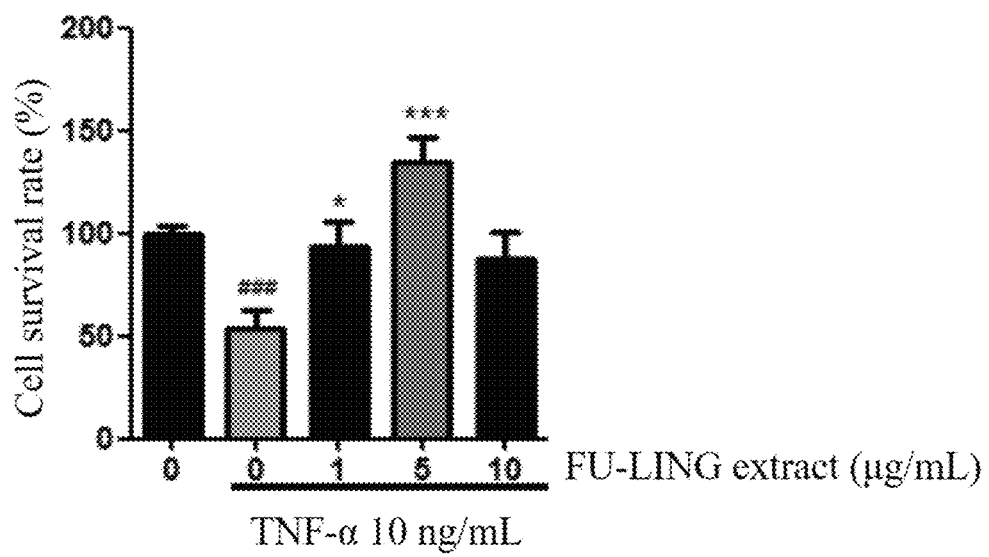
FIG. 2 illustrates the effects of the FU-LING extract on the survival rate of C2C12 cells with TNF-α induced injury.
Figure 3:
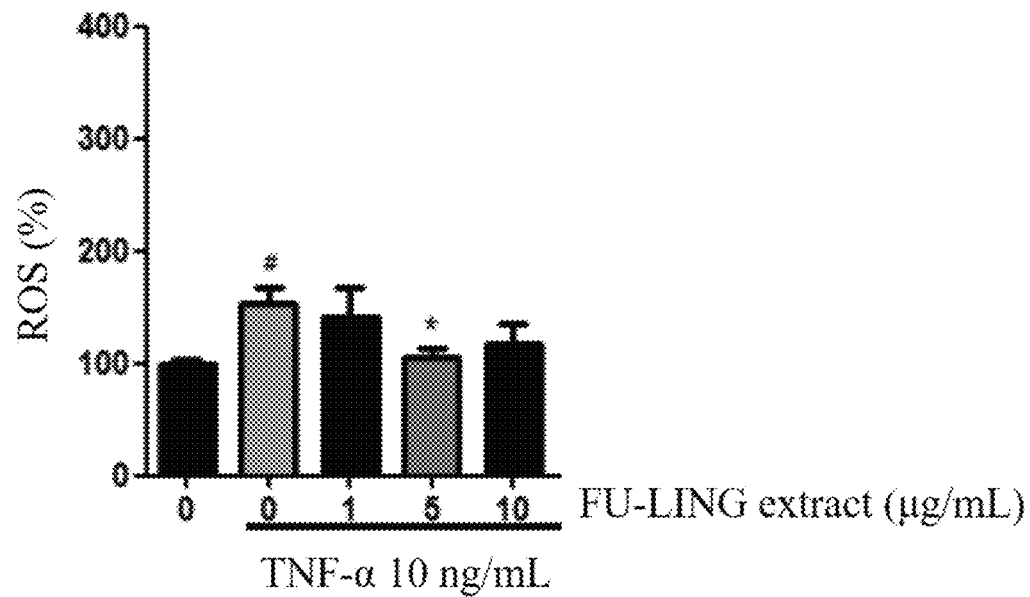
FIG. 3 illustrates the effects of the FU-LING extract on intracellular reactive oxidative stress of C2C12 cells with TNF-α induced injury.

As shown in FIGS. 2 and 3, in the TNF-α induced cell injury group, when cells were pre-treated with FU-LING extract ranging from 1 to 5 μg/mL, the survival rates of C2C12 cells gradually increased along with the increase in the concentration of FU-LING extract, while intracellular ROS of C2C12 cells gradually decreased along with the increase in the concentration of FU-LING extract. When cells were pre-treated with 5 μg/mL of FU-LING extract, the ROS decreased to be equivalent to that in the cells of the control group (without TNF-α induced injury). The above results indicate that the FU-LING extract can effectively decrease TNF-α induced muscle cell injury, and has the effect of protecting muscle cells against injury.

Example 4

Effects of the FU-LING Extract and Tumulosic Acid on Promoting the Regeneration and Repair of Muscles As described above, myogenin and MyHC can be used as markers for myoblast differentiation. To investigate whether FU-LING extract and tumulosic acid have the effect of promoting differentiation of myoblasts, tumulosic acid (purchased from Sinphar pharmaceutical co. ltd), FU-LING meat extract obtained from Example 1 (1-4), FU-LING epidermis extract obtained from Example 1 (1-6), and the FU-LING fermentation extract obtained from Example 1 (1-7) were formulated into the following: (1) tumulosic acid solution, (2) FU-LING meat extract solution, (3) FU-LING epidermis extract solution, and (4) FU-LING fermentation extract solution, respectively, in dimethyl sulfoxide (DMSO; purchased from Sigma Company).

After 80% confluence of cells was attained in H-DMEM medium, cells were separated into fourteen groups and treated as follows:
(1) Control group: The medium was replaced by a differentiation medium supplemented with 2% horse serum, and the cells were cultured for 4 days.
(2) Meat extract group (3 groups): The medium was replaced by a differentiation medium supplemented with 2% horse serum, and FU-LING meat extract solution was then added into the medium (the final concentration was 0.1, 1 or 10 ng/mL) to perform a co-treatment for 4 days.
(3) Epidermis extract group (4 groups): The medium was replaced by a differentiation medium supplemented with 2% horse serum, and FU-LING epidermis extract solution was then added into the medium (the final concentration was 0.01, 0.1, 0.5 or 1 ng/mL) to perform a co-treatment for 4 days.
(4) Fermentation extract group (3 groups): The medium was replaced by a differentiation medium supplemented with 2% horse serum, and FU-LING fermentation extract solution was then added into the medium (the final concentration was 0.2, 2, or 20 ng/mL) to perform a co-treatment for 4 days.
(5) Tumulosic acid group (4 groups): The medium was replaced by a differentiation medium supplemented with 2% horse serum, and tumulosic acid solution was then added into the medium (the final concentration was 0.01, 0.1, 1 or 10 ng/mL) to perform a co-treatment for 4 days.

After that, cell proteins in each group were extracted. Thereafter, the expression levels of myoblast differentiation markers (myogenin and MyHC) were detected by Western blot. Finally, the control group served as a basis (e.g., the expression level of the control group was 100%) for calculating the relative expression levels of myogenin and MyHC proteins in each group. The results are shown in Table 2.

TABLE 2

| Groups | | Expression level of myogenin (%) | Expression level of MyHC (%) |
|---|---|---|---|
| Control group | | 100 | 100 |
| Meat extract group (ng/mL) | 0.1 | 130 | 110 |
| | 1 | 100 | 120 |
| | 10 | 270 | 130 |
| Epidermis extract group (ng/mL) | 0.01 | 150 | 110 |
| | 0.1 | 180 | 140 |
| | 0.5 | 170 | 210 |
| | 1 | 140 | 220 |
| Fermentation extract group (ng/mL) | 0.2 | 170 | 160 |
| | 2 | 220 | 130 |
| | 20 | 160 | 190 |
| Tumulosic acid group (ng/mL) | 0.01 | 130 | 90 |
| | 0.1 | 130 | 80 |
| | 1 | 160 | 70 |
| | 10 | 490 | 180 |

As shown in Table 2, a low-dose (0.1 μg/ml) of FU-LING meat extract can increase the expression level of myogenin protein by about 30%, and a high dose (10 μg/ml) of FU-LING meat extract can increase the expression level of myogenin protein by up to 170%. A low-dose (0.01 μg/ml) of the FU-LING epidermis extract can increase the expression level of myogenin protein by about 50%, 0.1-0.5 μg/ml of FU-LING epidermis extract can increase the expression level of myogenin protein by about 70-80% and 1 μg/ml of FU-LING epidermis extract also increases the expression level of myogenin protein. A low-dose (0.2 μg/ml) of FU-LING fermentation extract can increase the expression level of myogenin protein by about 70%, 2 μg/ml of FU-LING fermentation extract can increase the expression level of myogenin protein by about 120%, and 20 μg/ml of FU-LING fermentation extract also increases the expression level of myogenin protein. A low dose (0.01-0.1 μg/ml) of tumulosic acid can increase the expression level of myogenin protein by about 30%. The expression level of myogenin protein increased along with the increase in the concentration of tumulosic acid, wherein 10 μg/ml of tumulosic acid increased the expression level of myogenin protein by about of about 390%.

Also as shown in Table 2, 10 μg/ml of FU-LING meat extract can increase the expression level of MyHC protein by about 30%; in another aspect, a low-dose (0.01 μg/ml) of the FU-LING epidermis extract can increase the expression level of MyHC protein by about 10%, and the expression level of MyHC protein increased along with the increase in the concentration of FU-LING epidermis extract, wherein 1 μg/ml of FU-LING epidermis extract can increase the expression level of MyHC protein by about 120%. A low-dose (0.2 μg/ml) of FU-LING fermentation extract can increase the expression level of MyHC protein by about 60%, and 20 μg/ml of FU-LING fermentation extract can increase the expression level of MyHC protein by up to 90%. 10 μg/ml of tumulosic acid can increase the expression level of MyHC protein by about 80%.

The results showed that FU-LING extract (including FU-LING meat extract, FU-LING epidermis extract, FU-LING fermentation extract, etc.) and tumulosic acid can both effectively enhance the expression levels of myoblast differentiation markers (myogenin and MyHC) in C2C12 cells, therefore, can provide the effect of promoting muscle cell differentiation, and are useful for helping the regeneration and repair to the injured muscle tissue.

As shown in the above experimental results, the FU-LING extract can effectively protect the injured muscle cells, thereby, increasing the muscle cell survival rate and inhibiting the increase of ROS simultaneously. Therefore, the FU-LING extract has the effect of ameliorating the oxidative stress of injured muscle cells. Additionally, the FU-LING extract and tumulosic acid contained therein can promote the differentiation of myoblasts, showing that the FU-LING extract and ingredients contained therein can effectively protect muscle cells against injury, promote the regeneration and repair of muscles. Thus, the FU-LING extract and ingredients contained therein can be used for protecting muscles, and are useful for helping normal muscle contraction, maintaining normal muscle physiology, maintaining normal neuromuscular function, maintaining normal energy metabolism, or enhancing energy level.

BRIEF DESCRIPTION OF REFERENCE NUMERALS

Not applicable

What is claimed is:

1. A method of protecting muscle cells against injury and/or promoting regeneration and repair of muscles in a subject in need thereof, comprising administering to a subject suffering from muscle cell or muscle tissue injury a composition consisting of:
    (a) an effective amount of a *Poria cocos* (FU-LING) extract; and
    (b) at least one of a toner, a buffer, a preservative, and a pharmaceutically acceptable carrier.

2. The method as claimed in claim 1, wherein the FU-LING extract is a polar solvent extract of FU-LING, and the polar solvent is selected from the group consisting of water, C1-C4 alcohols, and a combination thereof.

3. The method as claimed in claim 1, wherein the FU-LING extract comprises tumulosic acid.

4. The method as claimed in claim 1, wherein the FU-LING extract is an extract of the meat of the FU-LING, an extract of the epidermis of the FU-LING and/or an extract of a fermentation product of the FU-LING, wherein the fermentation product is obtained by inoculating a FU-LING strain in a solid matrix and then fermenting in the dark for several weeks to several months.

5. The method as claimed in claim 1, wherein the composition regulates, treats, and/or delays muscle atrophy caused by at least one of the following: aging, disease, and cachexia.

6. The method as claimed in claim 1, wherein the composition helps muscle contraction, maintains muscle physiology, maintains neuromuscular function, maintains energy metabolism, or enhances energy level.

7. A method of protecting muscle cells against injury and/or promoting regeneration and repair of muscles in a subject in need thereof, comprising administering to a subject suffering from muscle cell or muscle tissue injury a composition consisting of:
    (a) an effective amount of an active ingredient, wherein the active ingredient is tumulosic acid and/or a pharmaceutically acceptable salt of tumulosic acid, and
    (b) at least one of a toner, a buffer, a preservative, and a pharmaceutical acceptable carrier.

8. The method as claimed in claim 7, wherein the composition regulates, treats, and/or delays muscle atrophy caused by at least one of the following: aging, disease, and cachexia.

9. The method as claimed in claim 7, wherein the composition helps muscle contraction, maintains muscle physiology, maintains neuromuscular function, maintains energy metabolism, or enhances energy level.

* * * * *